United States Patent
Zedler et al.

(10) Patent No.: US 6,494,905 B1
(45) Date of Patent: Dec. 17, 2002

(54) BALLOON CATHETER

(75) Inventors: Stephan Zedler, Berlin (DE); Erik Trip, Grubo (DE); Hartmut Loos, Overisjse (BE)

(73) Assignee: Biotronik Mess und Therapiegerate GmbH & Co. Ingenieurburo Berlin, Berlin (DE)

(*) Notice: Subject to any disclaimer, the term of this patent is extended or adjusted under 35 U.S.C. 154(b) by 18 days.

(21) Appl. No.: 09/620,389

(22) Filed: Jul. 20, 2000

(30) Foreign Application Priority Data

Jul. 20, 1999 (DE) ......................... 199 34 923

(51) Int. Cl.⁷ .................................. A61F 2/06
(52) U.S. Cl. ...................... 623/1.11; 623/1.35
(58) Field of Search ................ 423/1.11, 1.35, 423/1, 12; 606/194, 108; 604/284, 285, 286, 915–921

(56) References Cited

U.S. PATENT DOCUMENTS

| | | | |
|---|---|---|---|
| 4,456,000 A | | 6/1984 | Schjeldahl et al. ........ 128/1 D |
| 5,613,980 A | * | 3/1997 | Chauhan ................ 623/1.11 |
| 5,672,153 A | | 9/1997 | Lax et al. ............... 604/22 |
| 5,720,735 A | * | 2/1998 | Dorros ................. 623/1.35 |
| 6,096,073 A | * | 8/2000 | Webster et al. ......... 623/1.16 |
| 6,117,117 A | * | 9/2000 | Mauch ................. 623/1.35 |
| 6,129,738 A | * | 10/2000 | Lashinski et al. ....... 623/1.35 |
| 6,165,195 A | * | 12/2000 | Wilson et al. .......... 623/1.35 |
| 6,258,073 B1 | * | 7/2001 | Mauch ................. 623/1.35 |
| 6,287,277 B1 | * | 9/2001 | Yan .................... 623/1.35 |

FOREIGN PATENT DOCUMENTS

| | | |
|---|---|---|
| DE | 39 15 289 A1 | 11/1990 |
| DE | 195 26 784 | 1/1997 |
| DE | 297 16 476 | 2/1998 |
| DE | 197 17 475 | 9/1998 |
| EP | 0 540 290 | 5/1993 |
| EP | 0 897 700 | 2/1999 |
| EP | 0 904 745 | 3/1999 |
| EP | 0 913 303 | 5/1999 |
| EP | 0 943 303 | 9/1999 |
| WO | WO 97/13471 | 4/1997 |
| WO | WO 99/15109 | 4/1999 |
| WO | WO 99/24104 | 5/1999 |
| WO | WO 99/36015 | 7/1999 |

* cited by examiner

Primary Examiner—Michael J. Milano
Assistant Examiner—(Jackie) Tan-Uyen T Ho
(74) Attorney, Agent, or Firm—Christie, Parker & Hale, LLP

(57) ABSTRACT

A balloon catheter for use in the region of a vessel branching and, in particular, in coronary vessels is provided. The catheter comprising a catheter stem disposed at the distal end of which are provided at least one balloon and at least one first guide means arranged in the region thereof for positioning the balloon in the region of a vessel branching. The first guide means is adapted to be introduced into the lateral branch of the vessel transversely with respect to the longitudinal direction of the balloon catheter. The balloon comprises at least two chambers which are spaced from each other in the longitudinal direction of the balloon catheter and between which the first guide means is arranged.

18 Claims, 5 Drawing Sheets

BALLOON CATHETER

FIELD OF THE INVENTION

The present invention relates, generally, to a balloon catheter for use in the region of vessel branchings and, in particular, in coronary vessels. More specifically, the present invention relates to a catheter comprising a catheter stem, at the distal end of which are provided at least one balloon and at least one first guide means which is arranged in the region of the balloon for positioning the balloon in the region of a vessel branching, wherein the first guide means is adapted to be introduced into the lateral branch of the vessel transversely with respect to the longitudinal direction of the balloon catheter.

BACKGROUND OF THE INVENTION

Balloon catheters are used for dilating constricted vessels in the human and animal body. The balloon, which is typically arranged at the distal end of the catheter stem, is generally introduced into the vessel system at a distance from the constriction and moved within the vessel system to the position of the constriction. The balloon is then expanded to enlarge the constriction by the action of pressure. Frequently, a tubular intraluminal support element, referred to as a stent, is arranged on the balloon such that it can be radially stretched and deformed upon expansion of the balloon. When the balloon is removed from the vessel, the stent remains in its radially deformed condition in the vessel thereby supporting the vessel in a permanently expanded state.

In a region containing vessel branchings and, in particular, for coronary vessels, it is necessary, particularly when a stent is to be implanted, for the balloon to be positioned as accurately as possible with respect to the vessel branching. For that purpose, a first guide means is typically provided, which is arranged in the region of the balloon and which, for the purposes of positioning the balloon in the region of a vessel branching, can be introduced into the lateral branch of the vessel transversely with respect to the longitudinal direction of the balloon catheter, thus serving as a positioning aid.

Such a balloon catheter is known in the prior art, such as, for example, from European patent application EP 0 904 745 A2, in which a guide wire which can be introduced into the lateral branch of the vessel is arranged along the outside of the balloon. This conventional balloon catheter design, however, suffers from the disadvantage that, upon expansion of the balloon, the guide wire, which is arranged on the outside of the balloon and which is surrounded by a guide tube, causes an irregular load to be applied to the vessel or the stent, if such is provided, in a peripheral direction. This irregular load is the result of the outwardly bulged configuration of the balloon in the region of the guide wire. The outwardly bulged configuration results in unwanted irregular deformation of the wall vessel or of the stent, which is disposed between the balloon and the wall of the vessel, in the peripheral direction. In this irregular deformed situation, relatively small radii of curvature, that is to say a relatively high degree of deformation, is induced in the region of the guide wire. This deformation can have a detrimental effect, not only on the weakened wall of the vessel, but also on the filigree structure of a stent. The stent structure may even suffer from local ruptures, which must be avoided.

A further disadvantage of the known balloon catheter lies in the relatively large transverse dimension of a balloon with a guide wire and a guide tube disposed on its outside surface.

Accordingly, there is a need for a balloon catheter which both provides the smallest possible transverse dimension for the balloon, and also ensures that the elements disposed therearound are deformed as uniformly as possible in the peripheral direction of the balloon upon expansion.

SUMMARY OF THE INVENTION

In accordance with the invention, a balloon catheter is provided for use in the region of vessel branchings and, in particular, of the coronary vessels. The balloon catheter of the present invention is designed to provide a uniform deformation of adjoining elements in the peripheral direction of the catheter upon expansion of the balloon. In one embodiment of the invention, the balloon catheter comprises a catheter stem, at the distal end of which are provided at least one balloon and at least one first guide means arranged in the region of the at least one balloon for positioning the balloon in the region of a vessel branching. In this embodiment the first guide means is adapted such that it may be introduced into a lateral branch of the vessel by extending the first guide means transversely with respect to the longitudinal direction of the balloon catheter.

Although the above embodiment is described in terms of a single balloon, it should be understood that the term balloon is used herein in a broad sense and is also intended to embrace any suitable arrangement of individually inflatable chambers. For example, in one embodiment of the present invention, the balloon has at least two inflatable chambers which are longitudinally spaced from each other along the length of the balloon catheter. In this embodiment the first guide means is arranged between the two chambers such that the outside of the balloon is not deformed by the presence of the first guide means. During operation of this embodiment, the substantially circular-cylindrical balloon is able to exert a substantially uniform deformation force and produce substantially uniform deformation in the peripheral direction.

In an alternative embodiment the balloon in accordance with the invention has at least two chambers which are longitudinally spaced from each other along the length of the balloon catheter. In this embodiment the first guide means can be arranged between the two chambers such that any guidance or feed means, such as, for example, a guide wire having a guide tube or hoze can be integrated into the stem of the catheter thereby allowing for a balloon catheter having a smaller transverse dimension.

As will be understood, the first guide means can take any form suitable for assisting with positioning of the balloon catheter into a lateral branch of a vessel, such as, for example, as a balloon which would extend into the lateral branch of the vessel upon expansion. In one alternative embodiment, the first guide means comprises a first guide wire. The first guide wire may be guided by any suitable means. In one embodiment of the invention the first guide wire is controlled through a mechanism in the catheter stem. In this embodiment a lateral exit for the guide wire would be provided in the catheter stem between the two inflatable chambers.

In another alternative embodiment of the invention a second guide wire is provided for guiding the balloon catheter in a longitudinal direction. In this embodiment the second guide wire can also be guided by a mechanism within the catheter stem, in which case the catheter stem is provided with a second guide wire exit means at its distal end.

In yet another alternative embodiment one or both of the guide wires can be provided with X-ray markers, such as, for example, an X-ray-opaque coating or the like in order to make it easier to monitor the positioning operation.

In still another preferred embodiment of the balloon catheter according to the invention, the first guide means is also adapted to deform support elements of a stent arranged in the region of a vessel branching such that the passage between the two vessel branches is opened.

In still yet another preferred embodiment of the balloon catheter according to the invention, the inflatable chambers are adapted to be filled separately.

In still yet another embodiment, the invention concerns a system for dilating constricted vessels and, in particular, coronary vessels, in the region of vessel branchings. The system comprising a balloon catheter according to the invention and a stent arranged on the balloon thereof. In this embodiment, the stent is provided with at least one branching portion arranged at the periphery of the peripheral casing of the stent in the region adjoining the first guide means. Also in this embodiment the branching portion of the stent may include at least one first support element which is provided for supporting the vessel transition in the region of a vessel branching and which can be pivoted substantially radially out of the peripheral surface and the first guide means is further adapted to pivot the support element of the peripheral surface. This provides a system for dilating constricted vessels, in the region of vessel branchings ensuring reliable dilation of the vessel including support for the transition into the branching-off branch of the vessel.

BRIEF DESCRIPTION OF THE DRAWINGS

Other embodiments and attendant advantageous of the invention are set forth in greater detail in the detailed description of the invention, with reference to the drawings, in which:

FIG. 1a is a cross-sectional view of an embodiment of the balloon catheter according to the invention;

FIG. 1b is a front cross-sectional view of an embodiment of the balloon catheter according to the invention;

FIG. 2a is a cross-sectional view of a system according to the invention for dilation of constricted vessels with an embodiment of the balloon catheter;

DETAILED DESCRIPTION OF THE INVENTION

Figure 1:
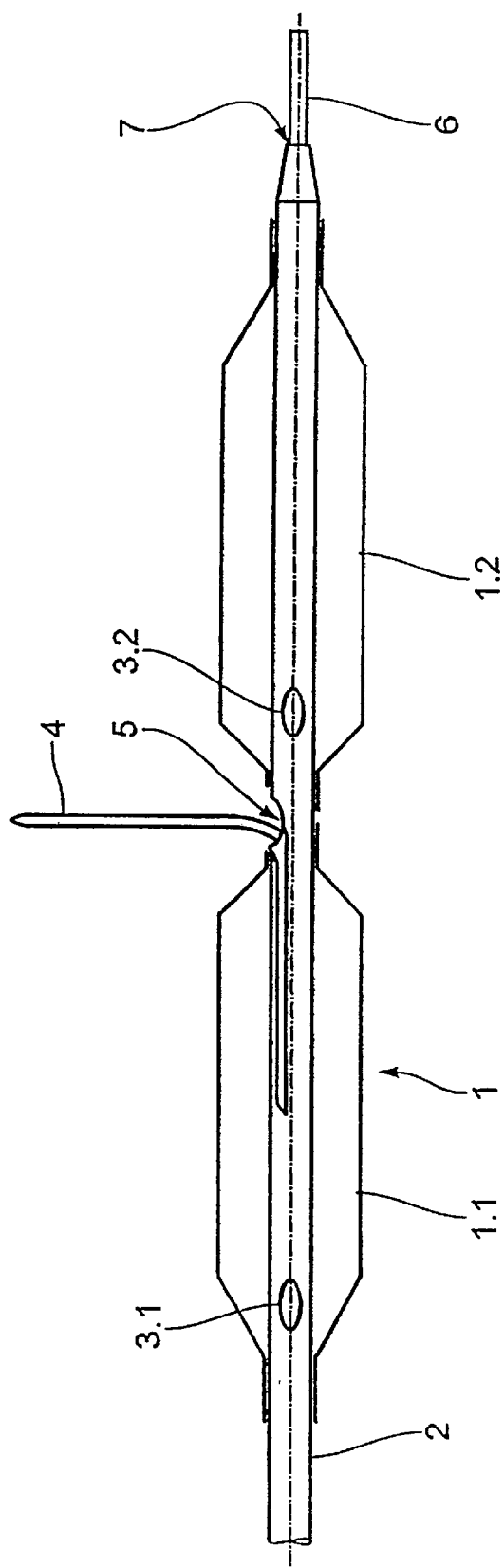
FIG. 1 is a cross-sectional view of an embodiment of the balloon catheter according to the invention.

FIG. 1 shows a balloon catheter 1 according to the invention, broadly comprising a balloon, which is arranged at the distal end of a catheter shank or stem 2. In this arrangement, the balloon comprises two inflatable chambers 1.1 and 1.2, which are longitudinally spaced from each other along the length of the balloon catheter 1. The inflatable chambers 1.1 and 1.2 can either be filled separately or simultaneously by way of filling openings 3.1 and 3.2 via at least one feed passage (not shown) disposed within the stem 2 of the catheter 1.

Although a balloon catheter 1 having two longitudinally arranged inflatable chambers 1.1 and 1.2 is shown in FIG. 1, it will be appreciated that any suitable arrangement of at least two inflatable chambers spaced longitudinally along the stem 2 of the catheter 1 may be utilized. It will also be appreciated that, in other alternative forms of the invention, a single filling opening or multiple filling openings supplied via a common feed passage can be utilized such that the two inflatable chambers 1.1 and 1.2 can be filled simultaneously.

A first guide wire 4 is also provided in the balloon catheter 1. In the embodiment shown the first guide wire 4 is disposed within the catheter stem 2 and exits the stem 2 laterally from a lateral exit opening 5 on the catheter stem 2 between the two inflatable chambers 1.1 and 1.2 of the balloon catheter 1. The first guide wire 4 may be arranged within the stem 2 of the catheter 1 in any geometry suitable, such as, for example, via a separate first guide wire lumen running within the stem 2 of the catheter 1 or alternatively via a single central lumen. During operation of the catheter 1, the first guide wire 4 can be utilized to position the inflatable chambers 1.1 and 1.2 in the region of a branch of a vessel which is to be dilated by means of the inflatable chambers 1.1 and 1.2. During such operation, the first guide wire 4 is extended in a direction transverse to the longitudinal direction of the stem 2 of the balloon catheter 1 laterally into a lateral branch of the vessel. The guide wire 4 can be provided with an X-ray-opaque coating such that its position within the vessel can be monitored. Alternatively, the guide wire may take the form of an expansive balloon.

The positioning of the first guide wire 4 within the catheter stem 2, and the positioning of the lateral exit opening 5 between the two chambers 1.1 and 1.2 of the balloon catheter 1 ensures that, upon expansion of the balloon 1 nothing is caught or jammed between the balloon and the vessel wall which is to be dilated or a stent which is to be expanded. This design avoids excessive local loadings or deformation in the stent or vessel to be dilated, which could result in damage to the parts to be dilated and which could tear the vessel wall or rupture the stent.

In the embodiment shown in FIG. 1, the balloon catheter also comprises a second guide wire 6 disposed within the catheter stem 2. In this embodiment, a distal exit opening 7 is provided at the distal end of the catheter stem 2 from which the second guide wire 6 issues. The second guide wire 6 can be extended from the catheter stem 2 through the distal exit opening 7 to provide longitudinal guidance to the balloon catheter 1. The second guide wire 6 is arranged within the catheter stem 2 in a second guide wire lumen through which the second guide wire 6 extends. The second guide wire may further include an X-ray opaque coating such that its position within the vessel can be monitored.

Figure 2:
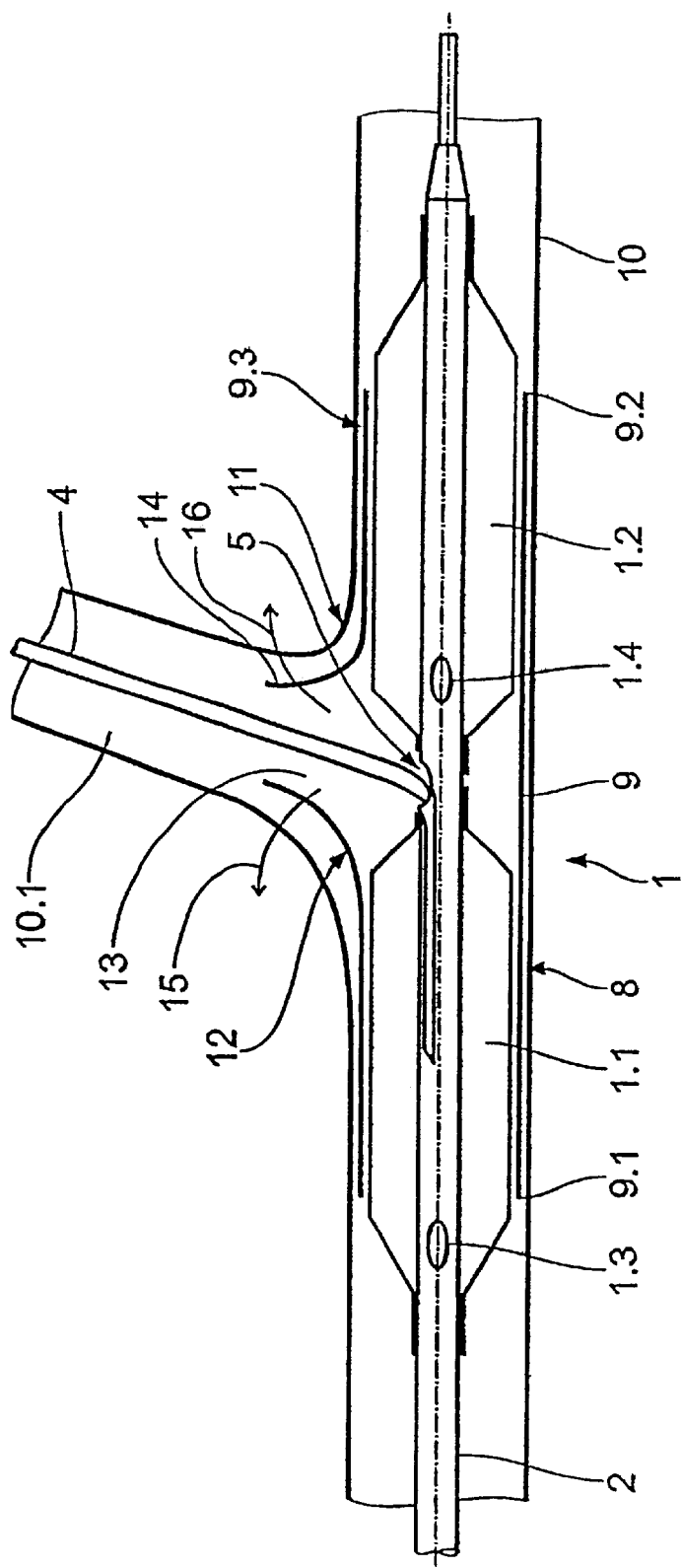
FIG. 2 is a cross-sectional view of a system according to the invention for the dilation of constricted vessels with the balloon catheter of FIG. 1.

FIG. 2 diagrammatically shows an embodiment of the catheter 1 according to the invention for dilating constricted vessels in the region of a vessel branching, comprising the balloon catheter of FIG. 1 and a stent 8 which is arranged coaxially on the balloon catheter 1. The stent 8, according to the embodiment shown in FIG. 2, comprises a tubular casing 9 with a proximal end 9.1 and a distal end 9.2. The stent 8 shown in FIG. 2 has been implanted in a blood vessel 10. In this implanted condition, the stent 8 is disposed in the region of a vessel branching 11, with its proximal end 9.1 arranged in proximal relationship with the vessel branching 11 and its distal end 9.2 arranged in distal relationship with the vessel branching 11. The stent 8 has a branch support portion 12, which when the stent 8 is implanted in the vessel 10 is arranged in the region of the vessel branching 11. To support the vessel branching region 11, the branch support portion 12 includes an elongated first support element 13 and an elongated second support element 14. In an initial condition of the stent (not shown here), the first support element 13 and the second support element 14 are disposed within the peripheral surface 9.3 of the casing 9 of the stent 8. When the stent 8 is activated, the first support element 13 extends in a first direction 15 into the vessel branching 11. That first direction 15 extends from the proximal end 9.1 of the stent 8 in parallel relationship with the longitudinal axis thereof. The second support element 14 extends in a second direction 16 which is opposite to the first direction, into the vessel branching 11, that is to say from the distal end 9.2 in parallel relationship with the longitudinal axis of the stent 8. The support elements 13 and 14 are curved radially out of the peripheral surface 9.3 into the lateral branch 10.1 of the vessel 10 by means of the first guide wire 4. When fully implanted, the first and second support elements 13 and 14 are extended flush against the wall of the vessel branching region 11 to support the same.

The casing 9 of the stent 8 can be designed in any known fashion such that the casing 9 can be deformed radially by means of the inflatable chambers 1.1 and 1.2 of the balloon catheter 1, and which remains in that condition after removal of the balloon catheter 1 so as to permanently dilate the vessel 10. For example, the casing 9 of the stent 8 may be constructed with a conventional plastically deformable grid-like bar structure.

In use of the above-described system for dilating constricted vessels 10, the procedure involved is preferably that described. Firstly, the stent 8, which is disposed on the balloon catheter 1, is positioned in the region of the vessel branch 11 in such a way that the branching portion 12 of the stent 8 is arranged in the region of the vessel branch 11. The balloon catheter 1 with at least one inflatable chamber 1.1 and 1.2 is used for that purpose and to assist in the positioning operation, the first guide wire 4 is passed through a suitable exit opening 5 in the stem 2 of the catheter 2 and then through a region of the branching portion 12 of the stent 8. The first wire guide 4 is then passed laterally out of the stent 8 and into the branch 10.1 of the vessel 10.

The inflatable chambers 1.1 and 1.2 are then expanded by way of the filling openings 1.3 and 1.4 disposed within the catheter stem 2. The inflatable chambers 1.2 and 1.2 may be expanded via any suitable technique, such as, for example, by introduction of a fluid which is subjected to the action of an external pressure 3. The introduction of the fluid would then cause expansion of the chambers 1.1 and 1.2 thereby dilating the stent 8 and deforming the stent casing 9 disposed around the balloon catheter 1 such that the stent 8 holds the vessel 10 in a permanently dilated condition after removal of the balloon catheter 1.

After expansion of the casing 9 of the stent 8, the support elements 13 and 14 are pivoted by means of the guide wire 4 radially out of the peripheral surface 9.3 of the casing 9 in the direction of the arrows 15 and 16 respectively into the branch 10.1 of the vessel 10, thereby supporting the wall of the vessel 10.1 in the region of the vessel branching 11.

Figure 3:
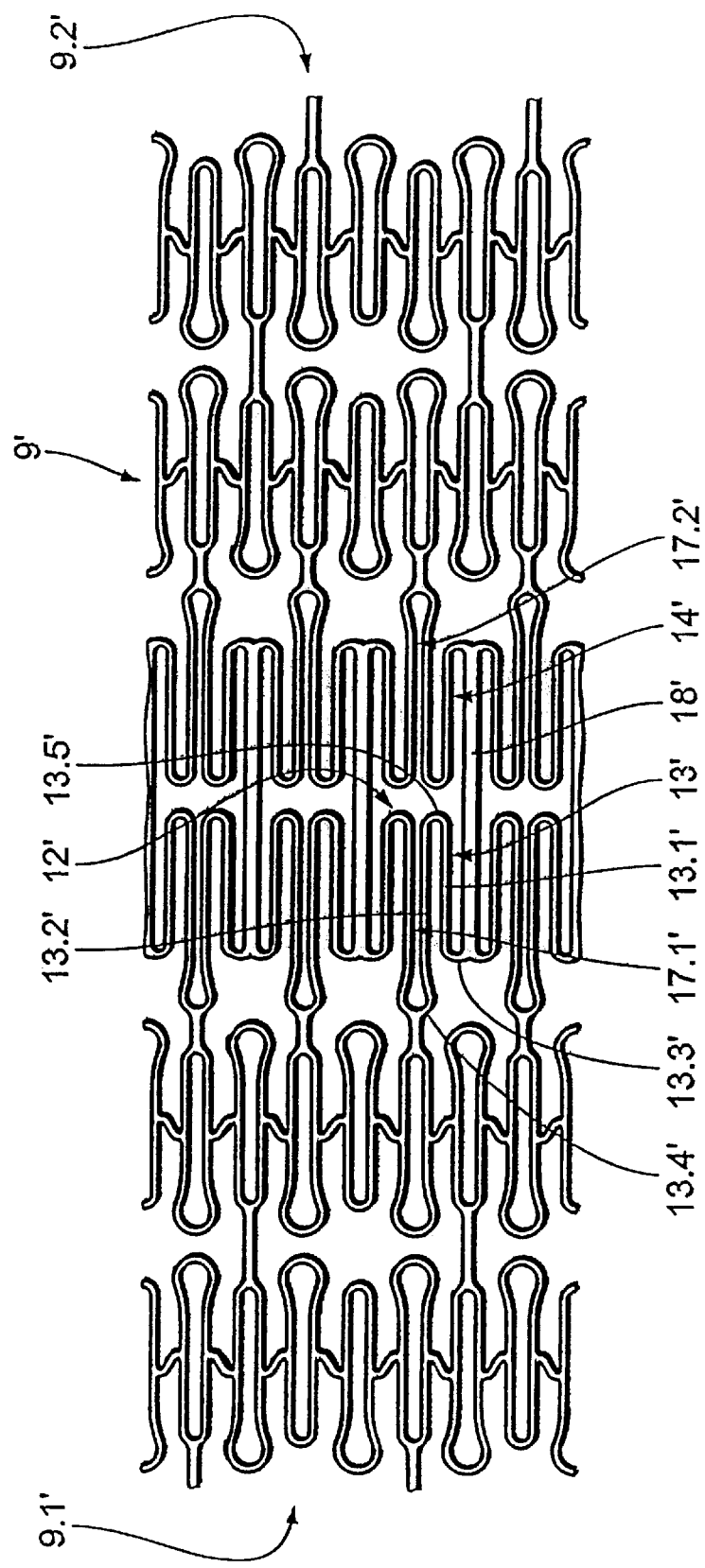
FIG. 3 is a schematic view of the peripheral surface of an embodiment of a stent for the system shown in FIG. 2.

While any suitable stent 8 design may be utilized in the current invention, FIG. 3 shows one embodiment of the casing 9' of a stent 8' for the system according to the invention as shown in FIG. 2. The casing shown in FIG. 3 comprises a structure of interconnected bar-like or web-like elements. In the embodiment shown in FIG. 3, the casing 9' has a number of branching portions 12' which are in mutually adjoining relationship in the peripheral direction of the casing 9'. Each branching portion 12' of the casing 9' includes a first support element 13', a second support element 14' arranged longitudinally along the casing 9', and a third and fourth support element 17.1' and 17.2' arranged adjacent to the first and second support elements 13' and 14' respectively in the peripheral direction of the casing 9'. In addition, the branching portion 12' is delimited in the peripheral direction of the casing 9' on both sides by a bar or web 18' extending longitudinally along the axis of the casing 9'. While the support elements 13', 14', 17.1' and 17.2' shown in the current embodiment are formed by hairpin shaped bar or web elements extending in the longitudinal direction of the casing 9', any suitable support features could be utilized to provide sufficient interconnectivity between the support elements. In the present embodiment, the hairpin bend region forms the free end of the respective support element 13', 14', 17.1' and 17.2'.

Figure 3A:
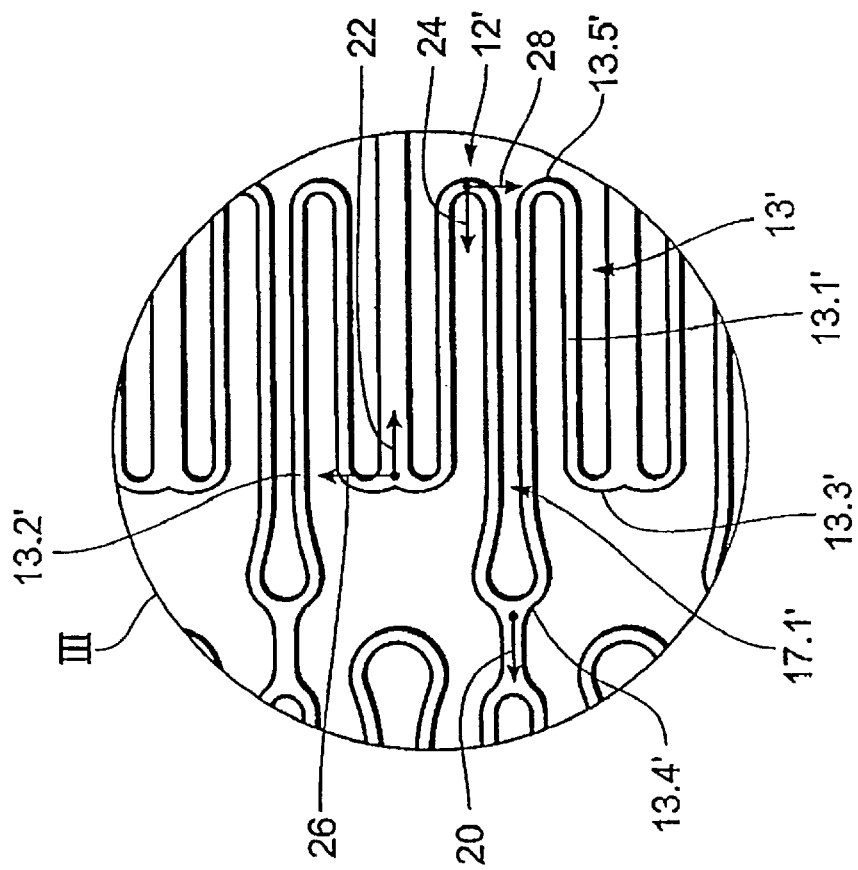
FIG. 3a is a detailed schematic view of the peripheral surface of an embodiment of the stent shown in FIG. 3.

Although any configuration and arrangement of the support elements 13', 14', 17.1' and 17.2' could be utilized such that they provide suitable structural support and interconnectivity between elements, in the embodiment shown in FIG. 3, the arrangement of the support elements 13', 14', 17.1' and 17.2' will be described with reference to the exemplary features of support element 13'. The limbs 13.1' and 13.21' of the support element 13' are connected to the bar 18' and to the casing 9' in such a way that the connecting points 13.3' and 13.4' move away from each other upon expansion of the stent 8' structure. In operation, as shown in FIG. 3a, the hairpin-like support element 13' in the peripheral surface of the stent 8' is pivoted open from the bend region 13.5', thus resulting in an increase in the size of the adjacent vessel region which can be supported thereby. As a result of the inherent interconnectivity of the support elements 13' and 17.1', and 14' and 17.2', this expansion and deformation of the support element 13' would also cause the free ends of the support elements 13' and 17.1', and 14' and 17.2' respectively to move away from each other in the peripheral direction, resulting in more uniform distribution of the support elements over the vessel wall 10 which is to be supported. In the embodiment shown in FIG. 3, the first limb 13.1', which is adjacent to the bar 18', is shorter than the second limb 13.2', which is adjacent to support element 17.1. As a result, the connecting points 13.3' and 13.4' are longitudinally separated from each other along the axis of the casing 9'. During operation, when the support elements 13', 14', 17.1' and 17.2' are pivoted about the connecting line of the connecting points 13.3' and 13.4' into the branch vessel 10.1, opening a passage 12 into the branching vessel 10.1. This passage is essentially adapted to the ellipsoidal contour of the branching vessel transition 11 and ensures uniform support for the branching vessel transition 11. In addition, by virtue of the inclination of the connecting line between the connecting points 13.31 and 13.4' with respect to the peripheral direction of the casing 9', the support elements 13', 14', 17.1' and 17.2', which are pivoted into the branch vessel 10.1' extend in the longitudinal direction of the branch vessel 10.1, providing support for the wall of branch vessel 10.1 over a relatively large peripheral region of the branch vessel 10.1.

Figure 4:
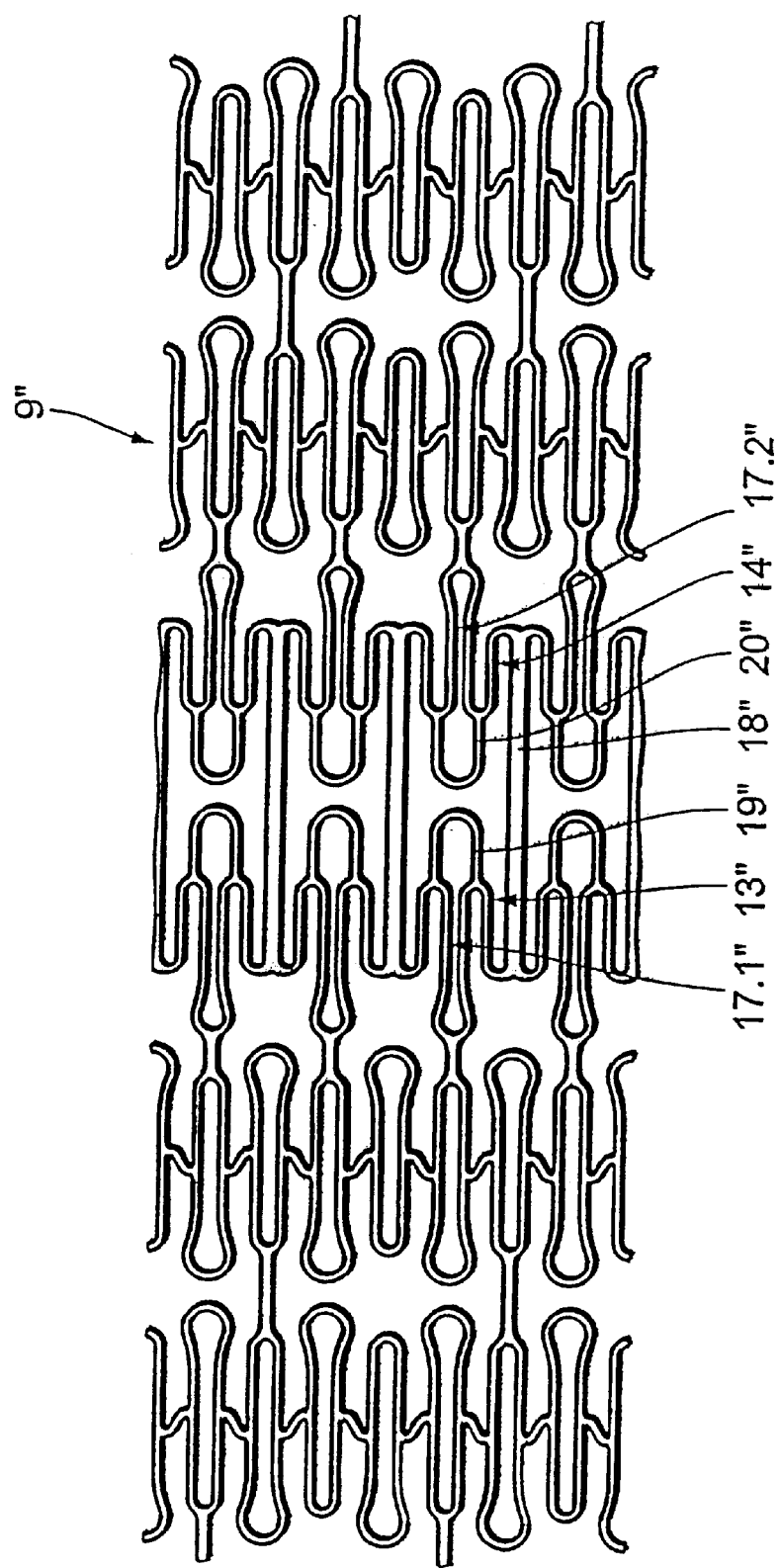
FIG. 4 is a schematic view of the peripheral surface of a further embodiment of a stent for the system in FIG. 2.

FIG. 4 shows another embodiment of the peripheral surface of a stent 8" for the system according to the invention as shown in FIG. 2. In this embodiment, the free ends of the support elements 13" and 17.1" are connected by way of a bar-like arcuate connecting element 19'" and the free ends of the support elements 14" and 17.2" are connected by way of a bar-like arcuate connecting element 20". In this embodiment, the arcuate connecting elements 19" and 20" respectively are of an arcuate length which is sufficient to compensate for a variation in spacing between the free ends of the support elements 13" and 17.1", 14" and 17.2" respectively upon expansion of the stent structure and subsequent pivotal movement of the support elements into the branch vessel 10.1. As such, in the pivoted condition, the connecting elements 19" and 20" then advantageously support the peripheral region of the vessel wall which is between the free ends of the support elements 13" and 17.1", 14" and 17.2" respectively.

The invention is not limited in terms of implementation thereof to the above-specified preferred embodiments. On the contrary, a number of alternative configurations are possible, which make use of the illustrated structure even in configurations of a basically different kind.

What is claimed is:

1. A balloon catheter for use in the region of vessel branchings comprising:

a catheter stem, defining an inner volume, and having a proximal and a distal end;

at least two inflatable chambers disposed longitudinally along the catheter stem proximate to the distal end of the catheter stem in fluid communication with a pressure source;

the catheter stem further comprising at least one lateral exit disposed between the at least two inflatable chambers; and at least one first guide wire being adapted to exit the catheter stem through the at least one lateral exit.

2. A balloon catheter as set forth in claim 1 comprising a second guide wire disposed within the inner volume adapted to extend longitudinally along the axis of the catheter stem.

3. A balloon catheter as set forth in claim 2 wherein the inner volume of the catheter stem comprises at least two lumens, and wherein the first guide wire is disposed within one of said lumens and wherein the second guide wire is disposed within the other of said lumens.

4. A balloon catheter as set forth in claim 2, wherein at least one of the first and second guide wires is coated with an X-ray marker.

5. A balloon catheter as set forth in claim 1 wherein the catheter further comprises a second guide wire adapted to extend longitudinally along the axis of the catheter stem.

6. A balloon catheter as set forth in claim 1 wherein the catheter further comprises a second guide wire and at least one distal exit opening at its distal end, and wherein the second guide wire is disposed within the inner volume of the catheter stem and is adapted to extend longitudinally along the axis of the catheter stem and through the at least one distal exit opening.

7. A balloon catheter as set forth in claim 1 wherein the external pressure source is disposed within the inner volume of the catheter stem.

8. A balloon catheter as set forth in claim 1 wherein the at least two inflatable chambers are adapted to be filled separately.

9. A balloon catheter as set forth in claim 1 wherein the at least two inflatable chambers are adapted to be filled simultaneously.

10. A balloon catheter as set forth in claim 1 further comprising a deformable stent for supporting a vessel wall positioned coaxially around the inflatable chambers on the catheter stem and adapted to radially deform upon application of an expansive force.

11. A balloon catheter as set forth in claim 10 wherein the deformable stent comprises a plurality of interconnected support elements.

12. A balloon catheter as set forth in claim 11 wherein the support elements take the form of a shape selected from the group consisting of: arcuate bars, hairpins, webs and bars.

13. A balloon catheter as set forth in claim 11 wherein the stent further comprises at least one branching portion arranged in the body of the stent, the branching portion comprising at least one support element, wherein the at least one support element of the branching portion of the stent is adapted to pivot radially out of the surface of the body.

14. A system for dilating constricted vessels in the region of vessel branchings comprising:

a balloon catheter comprising:
  a catheter stem, defining an inner volume, and having a proximal and a distal end;
  at least two inflatable chambers disposed longitudinally along the catheter stem proximate to the distal end of the catheter stem in fluid communication with a pressure source;
  the catheter stem further comprising at least one lateral exit disposed between the at least two inflatable chambers; and
  at least one first guide wire being adapted to exit the catheter stem through the at least one lateral exit;
a stent comprising a body defining an inner volume and an inner and outer surface, wherein the body is adapted to permanently expansively deform upon application of a force to the inner surface of the body, wherein the stent is arranged coaxially around the inflatable chambers of the catheter.

15. A system for dilating constricted vessels as set forth in claim 14 wherein the body comprises a plurality of interconnected support elements.

16. A system for dilating constricted vessels as set forth in claim 15 wherein the stent further comprises at least one branching portion arranged in the body, the branching portion comprising at least one branching support element, wherein the at least one branching support element is adapted to pivot radially out of the outer surface of the body.

17. A balloon catheter for use in the region of vessel branchings comprising:

a catheter stem, defining an inner volume and a single axis, and having a proximal and a distal end;

at least two inflatable chambers disposed longitudinally along the single axis proximate to the distal end of the catheter stem in fluid communication with an external pressure source;

the catheter stem further comprising at least one lateral exit disposed at the distal end of the catheter stem between the at least two inflatable chambers; and at least one first guide wire arranged to exit outward, transverse to the axis of the stem through the at least one lateral exit.

18. A balloon catheter for use in the region of vessel branchings comprising:

a catheter stem, defining an inner volume and a single axis, and having a proximal and a distal end;

at least two inflatable chambers disposed longitudinally along the single axis proximate to the distal end of the catheter stem in fluid communication with an external pressure source;

the catheter stem further comprising at least one lateral exit disposed at the distal end of the catheter stem between the at least two inflatable chambers; and at least one first guide wire being confined within the inner volume of the catheter stem, the first guide wire being adapted to extend outward, transverse to the axis of the stem through the at least one lateral exit.

\* \* \* \* \*